United States Patent [19]
Phillips et al.

[11] Patent Number: 5,122,596
[45] Date of Patent: Jun. 16, 1992

US005122596A

[54] POLYPEPTIDES USEFUL AS BLOCKERS OF CALCIUM CHANNELS

[75] Inventors: Douglas Phillips; Nicholas A. Saccomano, both of Ledyard; Robert A. Volkmann, Mystic, all of Conn.

[73] Assignee: Pfizer Inc., New York, N.Y.

[21] Appl. No.: 415,139

[22] Filed: Sep. 29, 1989

[51] Int. Cl.$^5$ .................. C07K 15/08; C07K 3/02; A61K 37/02
[52] U.S. Cl. .................. 530/350; 530/858; 514/21; 424/537; 424/538
[58] Field of Search .................. 514/21; 530/350, 858; 424/537, 538

[56] References Cited

U.S. PATENT DOCUMENTS 4,925,664  5/1990  Jackson et al. .................. 424/537

FOREIGN PATENT DOCUMENTS 8907608  8/1989  PCT Int'l Appl. .

OTHER PUBLICATIONS

Elvin A. Kabat, *Structural Concepts in Immunology and Immunochemistry*, 1976, p. 17.
Robert Berkow, Editor, *The Merck Manual*, 14th Edition, 1982, p. 279.
M. Toselli et al., *Neuroscience Letters* 112:70–75, 1990.
P. Dutar et al., *European Journal of Pharmacology* 174: 261–266, 1989.
K. A. Facklemann, *Science News* 139: 278, May 4, 1991.
Wayne S. Skinner et al., "Purification and Characterization of Two Classes of Neurotoxins from the Funnel Web Spider, *Agelenopsis aperta*", J. Biol. chem. 264: 2150–2155 (1989).
H. Jackson et al., "Spider Toxins as Tools for Dissecting Elements of Excitatory Amino Acid Transmission", Trends in Neuroscience 11: 278–283 (1988).
B. Cherksey et al., "Isolation of a Voltage Dependent Calcium Channel from the Squid Nervous System", Biophys. J. 55:438a (1989).
V. P. Bindokas et al., "ω-AGAI, A Spider Venom Toxin from *Agelenopsis aperta*, Irreversibly Blocks Transmitter Release at Insect and Frog Neuromuscular Junctions", Soc. Neuroscience Abstracts 14:30 (No. 17.11) (1988).
M. E. Adams et al., "Spider Venom Toxins Acting on Three Classes of Synaptic Ion Channels at the Insect Neuromuscular Junction", Soc. Neuroscience Abstracts 14:30 (No. 17.10) (1988).
M. Sugimori et al., "Spider Venom Blockade of Dendritic Calcium Spiking in Purkinje Cells Studied In Vitro", Soc. Neuroscience Abstracts 13:228 (No. 69.1) (1987).
H. Jackson et al., "Suppression of Chemically-Induced Behavioral Seizures in Rats by a Novel Spider Toxin", Soc. Neuroscience Abstracts 13:1078 (No. 300.6) (1987).
H. Jackson et al., "Presynaptic Blockade of Transmission by a Potent, Long-Lasting Toxin from *Agelenopsis*

*aperta* Spiders", Soc. Neuroscience Abstracts 12:730 (No. 197.4) (1986).
L. M. Kerr et al., "Effects of Spider Toxins on L and N CNS Calcium Channels: Inhibition and Enhancement of Binding", Soc. Neuroscience Abstracts 13: 102 (No. 31.15) (1987).
J. Hollis et al., "Effects of Spider Venom on Vertebrate CNS Glutamate Binding", Soc. Neuroscience Abstracts 13:756 (No. 209.3) (1987).
H. Jackson et al., "Spider Venoms Block Synaptic Transmission Mediated by Non-N-methyl-D-aspartate Receptors in the Avian Cochlear Nucleus", Soc. Neuroscience Abstracts 11:107 (No. 32.17) (1985).
R. Llinas et al., "Blocking and Isolation of a Calcium Channel from Neurons in Mammals and Cephalopods Utilizing a Toxin Fraction (FTX) from Funnel-Web Spider Poison", PNAS 86:1689–1693 (1989).
Nerotox '88 Molecular Basis of Drug & Pesticide Action, G. G. Lunt, Ed., Excerpta Medica, Amsterdam-New York-Oxford, 1988, Chapter 4, pp. 49–59.
V. P. Bindokas et al., "ω-Aga-I: A Presynaptic Calcium Channel Antagonist from Venom of the Funnel Web Spider, *Agelenopsis aperta*", J. Neurobiology 20:171–188 (1989).
B. C. Albensi et al., "Effects of Calcium Antagonist Peptide Spider Toxins on Hippocampal Synaptic Transmission Studied In Vitro", Soc. Neurosci. Abstr., 15:652 (No. 373.11) (1980).
L. D. Artman et al., "Peptide Toxins from *Agelenopsis aperta* Spider Venom Block Depolarization-Induced Increases in Cytosolic Free Calcium in Rat Cerebellar Granule Neurons", Soc. Neurosci. Abstr. 15:356 (No. 147.17) (1989).
J. W. Lin et al., "A Funnel-Web Spider Toxin (FTX) Fraction Blocks Calcium Currents Induced by Rat Brain mRNA in Xenopus Oocytes", Soc. Neurosci. Abstr. 15: 652 (No. 264.9) (1989).
H. Jackson et al., "Effects of Spider Venoms on Transmission Mediated by Non-N-Methyl-D-Aspartate Receptors in the Avian Cochlear Nucleus", Excitatory Amino Acid Transmission, 1987, Alan R. Liss, Inc., pp. 51–54.

(List continued on next page.)

*Primary Examiner*—Robert A. Wax
*Assistant Examiner*—Stephen Walsh
*Attorney, Agent, or Firm*—Peter C. Richardson; J. Trevor Lumb; D. Stuart McFarlin

[57] ABSTRACT

This invention relates to a polypeptide found to be present in the venom of the *Agelenopsis aperta* spider and to polypeptides having substantially the same amino acid sequence and substantially the same activity as said polypeptide. The polypeptides of this invention and the salts thereof block calcium channels in cells of various organisms and are useful in blocking said calcium channels in cells, per se; in the treatment of calcium channel mediated diseases and conditions; and in the control of invertebrate pests. This invention also relates to compositions comprising said polypeptides and salts thereof.

2 Claims, No Drawings

OTHER PUBLICATIONS

V. P. Bindokas et al., "Are Two Sub-Types of Presynaptic Calcium Channels Involved in Neurotransmitter Release at the Insect Neuromuscular Junction?", Soc. Neurosci. Abstr. 15:26 (No. 16.6) (1989).

J. M. Pocock et al., "Effects of ω-Agatoxins on Voltage-Dependent $CA^{++}$ Flux in Chick Brain Synaptosomes", Soc. Neurosci. Abstr. 15:652 (No. 264.7) (1989).

M. E. Adams et al., "ω-Agatoxins: A Family of Neuronal $Ca^{++}$ Channel Antagonists from Funnal Web Spider (*Agelenopsis aperta*) Venom", Soc. Neurosci. Abstr. 15:652 (No. 264.6) (1989).

POLYPEPTIDES USEFUL AS BLOCKERS OF CALCIUM CHANNELS

BACKGROUND OF THE INVENTION

1. Field of the Invention

This invention relates to a polypeptide found to be present in the venom of the *Agelenopsis aperta* spider and to polypeptides having substantially the same amino acid sequence and substantially the same activity as said polypeptide. The polypeptides and the pharmaceutically-acceptable salts thereof block calcium channels in cells including neuronal and muscle cells of various organisms including invertebrates and vertebrates. This invention also relates to the use of said polypeptides and their salts in blocking calcium channels in cells such as cells in the nervous and muscular system of an organism, per se; in the treatment of calcium channel mediated diseases and conditions in a mammal; and in the control of invertebrate pests. Further, this invention relates to compositions comprising said polypeptides and salts thereof.

2. General Background

It has been reported that the venom of the spider *Agelenopsis aperta* contains at least two toxins which affect calcium currents. Jackson, H., et al., Soc. Neu. Sci. Abstr. 12:1078 (1987). Those authors disclose a toxin, referred to therein as AG2, which has a molecular weight of less than 1,000 daltons and appears to suppress calcium currents in a broad range of tissues. Further, Jackson, H., et al., Soc. Neu. Sci. Abstr. 12:730 (1986) report another toxin from *Agelenopsis aperta* comprising a component of about 6,000 M.W. That toxin is reported to effect presynaptic blockade of transmission and it has been suggested that the toxin blocks calcium channels associated with the release of neurotransmitter.

Certain polypeptides found to be present in the venom of the *Agelenopsis aperta* spider are disclosed in U.S. patent application Ser. No. 07/346,181, filed Apr. 28, 1989, now abandoned. Those polypeptides are disclosed therein as blockers of calcium channels in cells and are described as follows according to fractions in which they were found:

Fraction G:
An amino-terminal amino acid sequence comprising:

H$_2$N—glu—lys—gly—leu—pro—glu—gly—ala—glu—cys—asp—gly—asn—glu—ser—asp—cys—lys—cys—ala—gly—gln—trp—ile—lys—cys—arg—cys—pro—trp—lys—trp—his—ile—thr—gly—glu—gly—pro—cys—thr—cys—glu—arg—gly—leu—lys—lys—thr—cys—ile—ser—lys—leu—ser—asp—pro—asn—arg—asn—glu—trp—leu—ser—; molecular weight for the entire polypeptide according to FAB MS: 7267.

Fraction H$_1$:

H$_2$N—ala—cys—val—gly—glu—asn—gln—gln—cys—ala—asp—trp—ala—gly—pro—his—cys—cys—asp—gly—tyr—tyr—cys—thr—cys—arg—tyr—phe—pro—lys—cys—ile—cys—arg—asn—asn—asn—CONH$_2$; FAB MS: 4198.

Fraction H$_2$:

H$_2$N—ala—lys—ala—leu—pro—pro—gly—ser—val—cys—asp—gly—asn—glu—ser—asp—cys—lys—cys—tyr—gly—lys—trp—his—lys—cys—arg—cys—pro—pro—lys—gly—his—phe—thr—gly—glu—; molecular weight for the entire polypeptide according to FAB MS: 5494.

Fraction I:

H$_2$N—asp—cys—val—gly—glu—ser—gln—gln—cys—ala—asp—trp—ala—gly—pro—his—cys—cys—asp—gly—tyr—tyr—cys—thr—cys—arg—tyr—phe—pro—lys—cys—ile—cys—val—asn—asn—asn—CONH$_2$; FAB MS: 4158.

Fraction J:
An amino-terminal amino acid sequence comprising:

H$_2$N—asp—glu—pro—cys—ile—pro—leu—gly—lys—ser—cys—ser—trp—lys—ile—gly—thr—pro—tyr—cys—cys—thr—his—pro—asp—asp—ala—; molecular weight for the entire polypeptide according to FAB MS: 5505.

Fraction K:

H$_2$N—glu—asp—asn—cys—ile—ala—glu—asp—tyr—gly—lys—cys—thr—trp—gly—gly—thr—lys—cys—cys—arg—gly—arg—pro—cys—arg—cys—ser—met—ile—gly—thr—asn—cys—glu—cys—thr—pro—arg—leu—ile—met—glu—gly—leu—ser—phe—ala—CONH$_2$; FAB MS: 5274.

Fraction L$_1$:
An amino-terminal amino acid sequence comprising:

H$_2$N—ile—val—gly—gly—lys—thr—ala—lys—phe—gly—asp—tyr—pro—trp—met—val—ser—ile—gln—gln—lys—asn—lys—lys—gly—gly—phe—asp—; approximate molecular weight for the entire polypeptide of about 20,000.

Fraction L$_2$:
A polypeptide having the following identifying characteristics:

(a) present in a fraction from crude venom of the *Agelenopsis aperta* spider which elutes off a C-18 Vydac®22 mm ×250 mm, 300 Å pore size, 10 μ particle size column using a flow rate of 15 ml/min., a solvent system using a linear gradient program of 5% →20% B, 95% →80% A [0 →30 min.]then 20% →70% B, 80% →30% A [30 →55 min.], where A is 0.1% aqueous TFA and B is acetonitrile, at about 43 minutes; and (b) present in a fraction of the fraction described in (a), above, which elutes off a C-18 Vydac®10 mm ×250 mm, 300 Å A pore size, 5 μ particle size column using a flow rate of 3.5 ml/min. and a solvent system using a linear gradient program of 25% →40% B, 75% →60% A [0 →30 min.], where A is 0.1% aqueous TFA and B is acetonitrile, at about 22.5 minutes.

Fraction M:
An amino-terminal amino acid sequence comprising:

H$_2$N—glu—ala—thr—glu—ala—ala—lys—val—leu—ser—asn—leu—asp—glu—thr—val—asp—pro—; approximate molecular weight for the entire polypeptide of about 80,000.

Compounds which are calcium antagonists have a variety of utilities. Calcium antagonists can find clinical application in the treatment of such conditions as angina, hypertension, cardiomyopathies, supraventricular arrhythmias, aesophogeal achalasia, premature labor and Raynaud's disease among others. See W. G. Nayler, *Calcium Antagonists*, Academic Press, Harcourt Brace Jovanovich Publishers, New York, NY 1988, the teachings of which are incorporated herein by reference. Further, such compounds are useful in the study of the physiology of cells such as neuronal and muscle cells and in the control of invertebrate pests.

SUMMARY OF THE INVENTION

This invention concerns a polypeptide found to be present in the venom of the *Agelenopsis aperta* spider. The polypeptide of this invention and the fraction in which it is present according to this invention is as follows:

Fraction Q:

(a) present in a fraction from crude venom of the *Agelenopsis aperta* spider which elutes off a C-18 Vydac ®22 mm ×250 mm, 300 Å pore size, 10 μ particle size column using a flow rate of 15 ml/min., a solvent system using a linear gradient program of 5% →20% B [0 →30 min.] then 20% →70% B [30 →55 min.], where A is 0.1% aqueous trifluoroacetic acid (TFA) and B is acetonitrile, at about 41.5 minutes;

(b) present in a fraction of the fraction described in (a), above, which elutes off a C-18 Vydac ®10 mm ×250 mm, 300 Å pore size, 5 μ particle size column using a flow rate of 3.5 ml/min., a solvent system using an isocratic system of 70%A, 30%B, where A is 0.1% aqueous TFA and B is acetonitrile, at 7.5 minutes; and (c) an amino-terminal amino acid sequence comprising:

H$_2$N—lys—lys—lys—cys—ile—ala—lys—asp—tyr—gly—arg—cys—lys—trp—gly—gly—thr—pro—cys—cys—arg—gly—arg—gly—cys—ile—cys—ser—ile—met—gl y—thr—asn—cys—glu—cys—lys—pro—arg—leu—ile—met—glu—gly—leu—.

The polypeptide of this invention blocks calcium channels in cells. Thus, said polypeptide is useful in blocking calcium channels in cells, per se. Said polypeptide is also useful in the control of invertebrate pests and in the treatment of diseases and conditions in a mammal mediated by calcium channel function in cells.

Also within the scope of this invention are polypeptides which have substantially the same amino acid sequence and substantially the same calcium channel blocking activity as the polypeptide described above.

This invention also concerns pharmaceutical compositions comprising said polypeptides and methods of administering said polypeptides.

DETAILED DESCRIPTION OF THE INVENTION

Venom is obtained from the *Agelenopsis aperta* spider through the process of milking by electrical stimulation according to standard methods well known to those skilled in the art. It is preferred that the method employed is one which safeguards against contamination of the whole venom by abdominal regurgitant or hemolymph. Such methods are well known to those skilled in the art. The whole venom so obtained is stored in a frozen state at about −78° C. until used for purification as described below.

Purification of the constituents from the whole venom is accomplished by reverse phase high performance liquid chromatography (HPLC) on a variety of preparative and semi-preparative columns such as C-4 and C-18 Vydac ® columns (Rainin Instrument Co. Inc., Mack Road, Woburn Ma. 01801). Peak detection is carried out monochromatically at 220–230 nm. Further analysis of the fractions can be accomplished with, for example, polychrome UV data collected with a Waters 990 diode array detector (Millipore Corporation, Waters Chromatography Division, 34 Maple Street, Milford, Ma. 01757). The fractions from the columns are collected by known methods such as through the use of an ISCO/"FOXY" fraction collector and an ISCO 2159 peak detector (ISCO, 4700 Superior, Lincoln, Ne. 68504). The fractions are collected in appropriately sized vessels such as sterile polyethylene laboratoryware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

The structures comprised by the respective fractions are determined according to known analytical methods such as by mass spectrometry and nuclear magnetic resonance. The polypeptide of Fraction Q is sequenced according to known methods. For example, S-pyridylethylation of cystine residues of the polypeptide under study can be performed in solution followed by amino acid sequencing of the polypeptide. One such procedure for S-pyridylethylation is as follows. About 1 to 10 μg of polypeptide is dissolved or diluted in up to 50 μl of a buffer prepared by mixing 1 part IM TrisHCl, pH 8.5 containing 4 mM EDTA and 3 parts 8M guanidine·HCl. Then, 2.5 μl of 10% aqueous 2-mercaptoethanol is added and the mixture is incubated at room temperature in the dark under argon for two hours. After incubation, 2 μl of 4-vinylpyridine (fresh reagent stored under argon at −20° C.) is added and the mixture is incubated for another two hours at room temperature in the dark under argon. The mixture is then desalted, preferably by chromatography on a short, reverse phase column. The recovered alkylated polypeptide is then sequenced according to known methods.

In practicing this invention and employing the general procedure outlined above, it has been found that a suitable column for initial fractionation of the venom is a C-18 Vydac ® 22 mm ×250 mm, 300 Å pore size, 10 μ particle size column. That column is eluted at a flow rate of 15 ml/min. using a linear gradient program of 95% →80% A, 5% →20% B [0 →30 min.]then 80% →30% A, 20% →70% B [30 →55 min.]where A is 0.1% aqueous trifluoroacetic acid (TFA) and B is acetonitrile. The fractions are collected as described above. A fraction so obtained, labeled Q', was chosen for further purification. The elution time of Fraction Q' was about 41.5 minutes.

Fraction Q' was subjected to further purification using a C-18 Vydac ®10 mm ×250 mm, 300 Å pore size, 5.0 μ particle size column at a flow rate of 3.5 ml/min. using an isocratic system of 70% 0.1% aqueous TFA, 30% acetonitrile. Fractions were collected as described above. Fraction Q eluted from the column at about 7.5 minutes. It was also found that a fraction which eluted at about 8.3 minutes contained a polypeptide which is described in U.S. patent application Ser. No. 07/346,181, now abandoned, as fraction K.

Fraction Q comprised a polypeptide having an amino-terminal amino acid sequence comprising:

H₂N—lys—lys—lys—cys—ile—ala—lys—asp—tyr—gly—arg—
cys—lys—trp—gly—gly—thr—pro—cys—cys—arg—gly—arg—
gly—cys—ile—cys—ser—ile—met—gly—thr—asn—cys—glu—
cys—lys—pro—arg—leu—ile—met—glu—gly—leu—.

Given the benefit of the disclosure herein with respect to the compound present in fraction Q of venom from *Agelenopsis aperta*, it is now possible to obtain said compound by methods other than through isolation/purification from whole venom. The polypeptide of this invention can be produced using recombinant DNA techniques through the cloning of a coding sequence for said polypeptide or portions thereof. For example, hybridization probes which take advantage of the now known amino acid sequence information of said polypeptide can be employed according to methods well known to those skilled in the art to clone a coding sequence for the entire polypeptide. A combination of recombinant DNA techniques and in vitro protein synthesis can also be employed to produce the polypeptides of this invention. Such in vitro protein synthesis methods include, but are not limited to, use of an ABI 430A solid phase peptide synthesizer (Applied Biosystems, Inc., 850 Lincoln Center Drive, Foster City, Ca. 94404) employing standard Merrifield chemistry or other solid phase chemistries well known to those skilled in the art.

It is well known in the art that certain amino acid substitutions can be made in polypeptides which do not affect, or do not substantially affect, the function of said polypeptides. The exact substitutions which are possible vary from polypeptide to polypeptide. Determination of permissible substitutions is accomplished according to procedures well known to those skilled in the art. Thus, all polypeptides having substantially the same amino acid sequence and substantially the same calcium channel blocking activity are within the scope of this invention.

The polypeptides of this invention irreversibly block calcium channels present in a variety of cells such as cells in the nervous and muscular system of invertebrates and vertebrates.

The ability of the polypeptides of this invention to block calcium channels is demonstrated by the following procedure. Cerebellar granule cells are prepared from the cerebellum of 8 day old rats (Wilkin, G. P. et al., Brain Res:115: 181-199, 1976). Squares (1 cm$^2$) of Aclar (Proplastics Inc., 5033 Industrial Ave., Wall, N.J., 07719) are coated with poly-L-lysine and placed in 12-well dishes that contain 1 ml of Eagles Basal Medium. The cells are dissociated and aliquots containing $6.25 \times 10^6$ cells are added to each well containing the squares of Aclar. Cytosine-beta-D-arabino furanoside (final concentration 10 $\mu$M) is added 24 hours post plating. The cells are used for fura2 analysis at 6, 7 and 8 days of culture. The cells (attached to the Aclar squares) are transferred to 12-well dishes containing 1 ml of 2 $\mu$M fura2/AM (Molecular Probes Inc., Eugene, OR, 97402) in HEPES buffer (containing 0.01% bovine serum albumin, 0.01% dextrose, pH 7.4, magnesium-free). The cells are incubated for 40 minutes at 37° C; the fura2/AM containing buffer is removed and replaced with 1 ml of the same buffer without fura2/AM. To a quartz cuvette is added 2.0 ml of prewarmed (37° C.) buffer. The cells on the Aclar are placed in the cuvette and the cuvette is inserted in a thermostated (37° C.) holder equipped with a magnetic stirrer and the fluorescence is measured with a fluorescence spectrophotometer (Biomedical Instrument Group, University of Pennsylvania). The fluorescence signal is allowed to stabilize for about two minutes. Then 5-20 $\mu$l of a stock solution of the compound under study in phosphate-buffered saline (PBS, pH 7.4) at appropriate concentrations are added to the cuvette. Calibration of the fluorescent signals and fura2/AM leakage correction are performed using the established procedures of Nemeth et al., J. Biol. Chem. 262:5188 (1987) at the completion of each test, the maximum fluorescence value (Fmax) is determined by addition of ionomycin (35 $\mu$M) and the minimum fluorescence value (Fmin) is determined by the subsequent addition of EGTA (12 mM) to chelate calcium. Employing the foregoing procedure, calcium channel blocking by a subject compound is shown to occur by a decrease in fluorescence upon addition of the subject compound.

The polypeptides of this invention are useful as calcium channel blockers in cells, per se. As such, these compounds are also useful in the control of invertebrate pests and in the treatment of diseases and conditions mediated by calcium channels function in cells in a mammal such as angina, hypertension, cardiomyopathies, supraventricular arrhythmias, aesophogeal achalasia, premature labor and Raynaud's disease. Further, these compounds are useful in the study of the physiology of cells including, but not limited to, cells of the nervous and muscular system.

Also within the scope of this invention are the pharmaceutically-acceptable salts of the polypeptides of this invention. Such salts are formed by methods well known to those skilled in the art. For example, base salts of the polypeptides can be prepared according to conventional methods.

When a polypeptide of this invention is to be administered to a mammal, it can be administered alone or in combination with pharmaceutically-acceptable carriers or diluents in a pharmaceutical composition according to standard pharmaceutical practice. The polypeptides can be adminstered orally or parenterally with the parenteral route of administration being preferred for the polypeptides. Parenteral administration includes intravenous, intramuscular, intraperitoneal, subcutaneous and topical administration.

For oral use of a polypeptide of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polypeptide or salt thereof of this invention is used in a human subject, the daily dosage will normally be determined by the prescribing physician. Moreover, the dosage will vary according to the age, weight and response of the individual patient, as well as the severity of the patient's symptoms and the potency of the particular compound being administered.

When a polypeptide or salt thereof of this invention is used in control of invertebrate pests, said polypeptide is administered to said invertebrate directly or provided to the environment of said invertebrate. For example, a compound of this invention can be sprayed as a solution onto said invertebrate. The amount of compound necessary for control of said invertebrate will vary according to the invertebrate and environmental conditions and will be determined by the person applying the compound.

When a polypeptide or salt thereof of this invention is used in the physiological study of cells, said polypeptide is administered to the cells according to methods well known to those skilled in the art. For example, said polypeptide can be administered to cells in an appropriate physiological buffer. An appropriate concentration of the compounds of this invention for use in such studies is 100 $\mu$M. However, the concentration of said polypeptide in such studies may be greater than or much less than 100 $\mu$M. The amount of the compound administered will be determined by the person skilled in the art according to well known methods.

The following Examples are illustrative and are not to be construed as limiting the scope of this invention.

EXAMPLE 1

Initial fractionation of whole venom of *Agelenopsis aperta*

Whole venom of *Agelenopsis aperta*, obtained from Natural Product Sciences Inc., Salt Lake City, Ut. 84108 and which had been stored in the frozen state at about $-78°$ C., was thawed and 10 to 60 $\mu$l amounts thereof, diluted to 200 $\mu$l and loaded onto a C-18 Vydac ®(22 mm ×250 mm, 300 Å pore size, 10 $\mu$particle size) column and eluted using a flow rate of 15 ml/min. and a solvent system using a linear gradient program of 5% →20% B, 95% →80% A [0 →30 min.] then 20% →70% B, 80% →30% A [30 →55 min.]where A is 0.1% aqueous TFA and B is acetonitrile. Peak detection was carried out monochromatically at 220–230 nm and fractions were collected with an ISCO/"FOXY" fraction collector and an ISCO 2159 peak detector. Fractions were collected from 20 minutes to 60 minutes. Fraction Q' was collected at about 41.5 minutes.

EXAMPLE 2

Subfractionation of fraction Q' and determination of structures therein

Fraction Q', obtained as described in Example 1, was loaded onto a C-18 Vydac ®(10 mm ×250 mm, 300 Å pore size, 5 $\mu$particle size) column and eluted therefrom using a flow rate of 3.5 ml/min. and an isocratic solvent system of 70% A, 30% B where A is 0.1% aqueous TFA and B is acetonitrile. Peak detection was accomplished using a Waters 990 diode array detector and fraction collection was accomplished as described in Example 1. Two fractions were obtained as follows:

| Fraction | Elution Time |
|---|---|
| Q | about 7.5 minutes |
| K | about 8.3 minutes |

Fractions Q and K, which comprises polypeptides, were then prepared for sequencing by lyophilization from the eluent followed by lyophilization from water, according to well known procedures.

Amino acid analysis of the alkylated polypeptide of fractions Q and K were obtained using the Waters Pico-Tag method according to manufacturer's specifications. Sequence data was collected from an Applied Biosystems model 470A Protein/Peptide sequencer (Applied Biosystems, Inc., 850 Lincoln Center Drive, Foster City, Ca. 94404) with aqueous TFA conversion. Analysis of the resulting phenylthiohydantoin amino acids was accomplished on line with an Applied Biosystems model 120A PTH analyzer or off line on a DuPont Zorbac PTH column (Biomedical Product Department, Chromatography Products. E. I. duPont de Nemours and Co., Inc., 1007 Ma-,.et Street, Wilmington, De. 19898).

As a result of amino acid analysis, the amino-terminal amino acid sequence of part of the polypeptide comprised by fraction Q was determined as:

H$_2$N—lys—lys—lys—cys—ile—ala—lys—asp—tyr—gly—arg—cys—lys—trp—gly—gly—thr—pro—cys—cys—arg—gly—arg—gly—cys—ile—cys—ser—ile—met—gl y—thr—asn—cys—glu—cys—lys—pro—arg—leu—ile—met—glu—gly—leu—.

As a result of amino acid analysis, it was also determined that fraction K comprised the polypeptide of fraction K described above and disclosed in U.S. patent application Ser. No. 07/346,181, now abandoned.

What is claimed is:

1. A substantially pure polypeptide having the following identifying characteristics:
   (a) present in a fraction from crude venom of the *Agelenopsis aperta* spider which elutes off a C-18 Vydac ® mm 33 250 mm, 300 Å pore size, 10 $\mu$particle size column using a flow rate of 15 ml/min. and a solvent system using a linear gradient program of 5% →20% B, 95% →80% A [0 →55 min.], where A is 0.1% aqueous TFA and B is acetonitrile, at about 41.5 minutes;
   (b) present in a fraction of the fraction described in (a), above, which elutes off a C-18 Vydac ®10 mm 33 250 mm, 300 Å pore size, 5 $\mu$particle size column using a flow rate of 3.5 ml/min. and an isocratic solvent system of 70% A, 30% B, where A is 0.1% aqueous TFA and B is acetonitrile, at about 7.5 minutes; and
   (c) an amino-terminal amino acid sequence comprising:

H$_2$N—lys—lys—lys—cys—ile—ala—lys—asp—tyr—gly—arg—cys—lys—trp—gly—gly—thr—pro—cys—cys—arg—gly—arg—gly—cys—ile—cys—ser—ile—met—gly—thr—asn—cys—glu—cys—lys—pro—arg—leu—ile—met—glu—gly—leu—;

or a polypeptide having substantially the same amino acid sequence and substantially the same calcium channel blocking activity as said polypeptide or a pharmaceutically-acceptable salt thereof.

2. The polypeptide according to claim 1 having the following characteristics:
   (a) present in a fraction from crude venom of the *Agelenopsis aperta* spider which elutes off a C-18 Vydac ®22 mm ×250 mm, 300 Å pore size, 10 $\mu$particle size column using a flow rate of 15 ml/min. and a solvent system using a linear gradient program of 5% →20% B, 95% →80% A [0 →30 min.] then 20% →70% B, 80% →30% A [30

→55 min.], where A is 0.1% aqueous TFA and B is acetonitrile, at about 41.5 minutes;

(b) present in a fraction of the fraction described in (a), above, which elutes off a C018 Vydac ®22 mm 33 250 mm, 300 Å pore size, 5 µparticle size column using a flow rate of 3.5 ml/min. and an isocratic solvent system of 70% A, 30% b, where A is 0.1% aqueous TFA and B is acetonitrile, at about 7.5 minutes; and (c) an amino-terminal amino acid sequence comprising:

H$_2$N—lys—lys—lys—cys—ile—ala—lys—asp—tyr—arg—
cys—lys—trp—gly—gly—thr—pro—cys—cys—arg—gly—arg—
gly—cys—ile—cys—ser—ile—met—gly—thr—asn—cys—glu—
cys—lys—pro—arg—leu—ile—met—glu—gly—leu—;

or a pharmaceutically-acceptable salt thereof.

* * * * *

UNITED STATES PATENT AND TRADEMARK OFFICE
CERTIFICATE OF CORRECTION

PATENT NO. : 5,122,596
DATED : June 16, 1992
INVENTOR(S) : Douglas Phillips et al.

It is certified that error appears in the above-identified patent and that said Letters Patent is hereby corrected as shown below:

Column 1, line 65, after "Fraction $H_2$", insert --An amino-terminal amino acid sequence comprising:--.

Column 2, line 54, replace "Å A" with --Å--.

Column 4, line 33, replace "IM" with --1M--.

Col. 8, claim 1, line 5, replace "mm 33" with --22 mm x--.
Col. 8,
Claim 1, line 8, insert --30 min.] then 20%→70% B, 80%→30% A [30→-- between "[0→" and "55 min.]".
Col. 8,
Claim 1, line 13, replace "33" with --x--.
Col. 9,
Claim 2, line 13, replace "CO18" with --C-18--.

Col. 9, claim 2, line 14, replace "33" with --x--.

Signed and Sealed this

Twenty-sixth Day of October, 1993

Attest:

BRUCE LEHMAN

*Attesting Officer*   *Commissioner of Patents and Trademarks*